(12) United States Patent
Sanpera Trigueros et al.

(10) Patent No.: US 10,548,640 B2
(45) Date of Patent: Feb. 4, 2020

(54) FIXATION SYSTEM FOR SPINAL INSTRUMENTATION

(71) Applicants: Ignacio Sanpera Trigueros, Baleares (ES); Jesús Burgos Flores, Madrid (ES)

(72) Inventors: Ignacio Sanpera Trigueros, Baleares (ES); Jesús Burgos Flores, Madrid (ES)

( * ) Notice: Subject to any disclaimer, the term of this patent is extended or adjusted under 35 U.S.C. 154(b) by 25 days.

(21) Appl. No.: 15/568,498

(22) PCT Filed: Apr. 23, 2015

(86) PCT No.: PCT/ES2015/070343
§ 371 (c)(1),
(2) Date: Oct. 23, 2017

(87) PCT Pub. No.: WO2016/170199
PCT Pub. Date: Oct. 27, 2016

(65) Prior Publication Data
US 2018/0140333 A1  May 24, 2018

(51) Int. Cl.
*A61B 17/70* (2006.01)
*A61B 17/88* (2006.01)

(52) U.S. Cl.
CPC ...... *A61B 17/7032* (2013.01); *A61B 17/7035* (2013.01); *A61B 17/7091* (2013.01); *A61B 17/8875* (2013.01)

(58) Field of Classification Search
CPC ............ A61B 17/7032; A61B 17/7035; A61B 17/8875
See application file for complete search history.

(56) References Cited

U.S. PATENT DOCUMENTS

| 5,782,833 | A | 7/1998 | Haider | |
|---|---|---|---|---|
| 2002/0010467 | A1 | 1/2002 | Cooper et al. | |
| 2007/0055242 | A1* | 3/2007 | Bailly | A61B 17/7032 606/266 |
| 2007/0288004 | A1 | 12/2007 | Alvarez | |
| 2008/0154315 | A1* | 6/2008 | Jackson | A61B 17/7035 606/309 |
| 2009/0318973 | A1* | 12/2009 | Moulin | A61B 17/6466 606/278 |

(Continued)

FOREIGN PATENT DOCUMENTS

| ES | 2302115 T3 | 7/2008 |
|---|---|---|
| ES | 2455122 T3 | 4/2014 |

(Continued)

OTHER PUBLICATIONS

International Search Report for PCT/ES2015/070343 dated Jan. 15, 2016.

*Primary Examiner* — Christian A Sevilla
(74) *Attorney, Agent, or Firm* — Brown & Michaels, PC

(57) ABSTRACT

A fixation system for spinal instrumentation comprising a cap (1), which houses the head of a screw (2), the end of said screw (2) projecting through a lower opening of said cap (1). A coupling element (3) having two tabs (33) on both side ends rests on the upper part of the head of said screw (2). Said coupling element (3) houses therein an adjusting ring (4) secured to a series of tabs (7), by which means the movement of the head of said screw (2) can be limited.

8 Claims, 13 Drawing Sheets

(56) References Cited

U.S. PATENT DOCUMENTS

| | | | |
|---|---|---|---|
| 2010/0152787 A1 | 6/2010 | Walsh et al. | |
| 2014/0031880 A1* | 1/2014 | Biedermann | A61B 17/8605 |
| | | | 606/305 |
| 2014/0222080 A1* | 8/2014 | Biedermann | A61B 17/7028 |
| | | | 606/270 |

FOREIGN PATENT DOCUMENTS

| | | |
|---|---|---|
| ES | 2525046 T3 | 12/2014 |
| MX | 2011000917 A | 4/2011 |
| WO | 03015648 A1 | 2/2003 |
| WO | 2007141347 A1 | 12/2007 |
| WO | 2009014540 A1 | 1/2009 |
| WO | 2009055400 A1 | 4/2009 |
| WO | 2014037093 A1 | 3/2014 |

\* cited by examiner

FIXATION SYSTEM FOR SPINAL INSTRUMENTATION

OBJECT OF THE INVENTION

The present invention patent aims to present a new fixation system for spinal instrumentation, based on a screw capable of limiting the movements in each and every one of the directions of the currently usable screws, being able to vary from a fixed screw to a polyaxial or uniaxial screw, in either of the sagittal or coronal directions.

This new fixation system for spinal instrumentation has a special application in the field of spinal surgery, where due to the circumstances, it is necessary to have a device with said characteristics.

BACKGROUND OF THE INVENTION

In the current state of the art, there are different documents that are described and analyzed below.

The invention patent (WO 2014037093 A1) discloses a system for a global three-dimensional correction of the curvatures of the spine, in which the fixation devices or pedicle screws are not polyaxial, since it uses uniaxial screws in different directions to correct the spine; however, it uses different screws on both sides and it does not mention a screw that can acts as a polyaxial, uniaxial or fixed screw.

The document ES 2455122 T3 describes a bone anchoring device comprising a receiving part to house a rod that engages a bone anchoring element that has a shank and a head, the bone anchoring element being a polyaxial screw wherein the head is clamped from the side to fix the rotational position of the bone screw and wherein a locking element is provided to secure the rod in the receiving part.

The aim is to provide an improved receiving part consisting of few parts and that is better handled during the surgical operation. Specifically, the receive the rod (6) and a housing space (19) for accommodating a head (3) of the bone anchoring element (1), the housing space (19) that has an opening (18) for introducing the head, and a pressure element (8) located at least in part in the housing space (19), the pressure element have a flexible part (82) for holding the head; wherein the pressure element (8) can adopt in the body of the receiving part (5) an insertion position wherein it is possible to introduce the head, a locking position wherein the head is locked in the receiving part and a pre-locking position wherein the head is fixed by the pre-tension exerted by the pressure element, and in which the pressure element (8) is maintained in the pre-locking position by means of an elastic force, the elastic force being generated by a spring part (9a, 9b, 92) in the pressure element or in the body of the receiving part that works with a stop (93) in the body of the receiving part (5) or the pressure element, respectively, the stop acting as a stop to ensure the pre-locking position; said intention describes a polyaxial screw that can be locked at a predetermined point, unlike the present invention, which once locked does not allow movement in any direction. The present invention is characterized either by converting the screw into a conventional fixed screw or, in the position that is locked, allowing the movement on only a coronal or sagittal axis. The aim of the present invention is not to achieve a screw that can be locked in a fixed position, but rather obtain, with a single screw, all the options that exist in the market of screws that are moveable in different directions and that are fixed, greatly simplifying the task and obtaining a screw with greater versatility; furthermore, after implementation, it allows a polyaxial screw to convert into a fixed or uniaxial screw.

The document ES 2525046 T3, of the same applicant as the previous document, describes a bone anchoring system including an anchoring element (1) with a shank (2) for anchoring it to the bone and a head (3), a housing part (5) that has an upper end (5a) and a lower end (5b), a channel (11) to house a rod (6) near the upper end and a housing space (9a, 9b) to house the head near the lower end, the housing space having an opening (10) towards the lower end that is sized to allow the introduction of the head (3) from the lower end; a pressure element (8) that is located at least partly in the housing space and that has a flexible part (85) for immobilizing the head; the anchoring element being able to rotate with respect to the housing part and being fixed at an angle by moving the pressure element inside the housing space such that the head (3) is locked inside the flexible part (85) of the pressure element, wherein the pressure element includes a protrusion (83, 83', 83") that engages an inlet section (9b, 13), that has an enlarged diameter in the housing part, when the pressure element is inserted into the housing part to prevent the loss of the pressure element from the housing part, and an inlet (11c) being provided in the bottom of the inlet (11c) channel (11) that is configured to engage the protrusion (83, 83', 83"), such that when the pressure element is inserted into the housing part with the protrusion (83, 83', 83") pointing to the inside of the channel (11), the protrusion (83, 83', 83") reaches the inlet section (9b, 13) through the inlet (11c), and in this situation, the pressure element can rotate inside the housing part.

Said document describes a system similar to the previous systems, which works as a polyaxial system and wherein the screw head is locked by means of an insert, the insert surrounds the head and upon closing, it closes on the head, clamping it. The system permits the entry of the screw head from inside the cap, as well as from the lower end of the cap. Like the other aforementioned cases, this screw always acts as a polyaxial screw until it is locked. The ring of the present invention along with the tabs secured to it act on the screw before the system is closed (introduction of the reducing bar and closure with the top) and its function is to lock movement in a specific direction, or in all directions (or it does not lock). Once the reducing bar is introduced and it is fixed with the closing lid, the system is locked by the pressure of the coupling element on the screw head, being fixed at that point.

The document WO 2009055400 A1 discloses a polyaxial screw assembly for insertion into the spinal region of the patient, which includes a pedicle screw (110), a coupling element (130), a threaded part (50) and a case or cap (70). The pedicle screw includes a shank that has a helical thread and a head at one end. The coupling element is placed on the upper part of the pedicle screw and releasably engages portions of the screw head. The coupling element and the pedicle screw are positioned inside a distal portion of the cap. The pedicle screw is slid through an opening in the threaded part and is thread into the distal portion of the cap to retain the coupling element and the pedicle screw inside the cap. The pedicle screw is rotatable and pivotable with respect to the cap. Compressing the coupling element inside the cap locks the pedicle screw, which is easily secured in a desired orientation.

Said invention uses a polyaxial screw system capable of being locked in a specific position, unlike the present invention, which does not explicitly seek to lock the screw in a specific position, but rather aims to have the screw work in different directions according to the necessary demands.

The document WO 2007141347 A1 discloses a vertebral fixation device fundamentally consisting of a pedicle screw (1) with a partially spherical head (2), a rosette (3, 3', 3") provided with an upper promontory (4) from which flexible slats (5) come down to press on and fix the position of the head with a specific orientation, a tulip (6) with lateral notches (7) opposite each other and a lower cavity (18) that holds the rosette, a bar (8) that constitutes the link with the other devices fixed to other vertebrae, which is housed in the lateral notches (7) and which rests against the upper head of the rosette (3, 3', 3"), a closing lid (9) with circular openings (10) through which the bar passes, which moves in an axial direction on the outer face of the tulip, and a closing screw (11) which is threaded on the inside the tulip (6) and drags the closing lid (9) along with it in its movement and fixes the bar (8) against one or more of the upper promontories of the rosette; similar to all the preceding systems, said system describes a screw that is not completely polyaxial and which seeks to successfully fix the screw at a specific point.

The document MX 2011000917 A discloses locking mechanisms (100) and methods of fixation, such as the fixation of a fixation device (104) like a bone screw and a rod (106) to the spine. The locking mechanism comprises a body (102) having a lower portion and a side portion, in which the side portion is configured to receive a rod (106); a fixation device (104) extending at least partially through a hole in the lower portion of the body; and a rod seat (110) between the rod and the fixation device, the rod seat having an upper portion configured to interact with the rod and a lower portion configured to receive part of the fixation device (104), specifically the spherical head (140) thereof, and an adjusting screw (112), in which the rod seat (110) is configured to be separated into two parts (110a-110b) when the rod (106) exerts force on the upper portion of the rod seat (110) and the fixation device (104) limits the movement of the rod seat towards the lower position of the body (102).

Said document reflects a polyaxial screw system that is locked in a fixed position by the pressure of the different coupling parts such that once the (closed) system is locked, the screw remains fixed in a position. The system is similar to that of the present invention in that it locks the screw by means of a coupling element; however, the fundamental difference is in what happens before locking. The function of the tabs in our screw is to lock the movement in specific directions (or in none) such that the screw supports certain stresses but not others (by having freedom of movement on some planes), and here the difference lies in the movement of the screw during the implementation of the reducing bar that connects the different vertebrae, since once the system has been closed and the reducing bar is properly placed, the system is locked with the screw fixed in that direction.

The document WO 2009014540 A1, which shares one of its inventors with the previous document and is similar thereto, discloses a locking mechanism (100) such as that of the previous patent, which adds an insert (108), such that the locking mechanism (100) has a fixation device (104) extending through a hole (118) of a main body (102), which has a side portion (120) that receives a rod (106). The partially spherical insert (108) surrounds the head (140) of the fixation device. A rod seat (110) has an opening for engaging an upper surface of the insert, and it applies forces to the insert that have both lateral and vertical components which will be applied to the head of the fixation device.

In this case, the rod seat (110) and insert (108) parts, which are engageable, have some similarity to the coupling element (3) and the adjusting ring (4), except for the pressure that causes the closure of the insert on the head thereof, since it locks the head and prevents the movement thereof. As in the other systems described, the mechanism seeks to lock the screw in a position to prevent the movement of the screw-reducing bar assembly. This is also achieved in the present invention when the reducing bar has closed inside the screw, even though the insert does not impede the movement, but rather limit movement in a certain direction when needed or allow it to move in all directions if necessary. The locking of the screw is only the final part, but that characterized in the present invention is the limitation of the movement of the screw in certain directions.

In the document ES 2302115 T3, an embodiment is shown in which an implant for locking a screw at any angle comprises a screw head retaining insert (84') that comprises a partially spherical seat (96). The outer wall of the insert element (84') is in the form of outwardly tapering tabs (98) that have an inwardly tapered inner wall (100). The insert element has a recess (102) which allows for the hinging or collapsing of the insert element about its diameter. The rod retaining ring (12''') comprises a cylindrical opening (104) and a seat for said insert, including axially extending slots (106) for receiving the outwardly tapering tabs (98). Thus, alignment means for aligning the insert element with respect to its seating position within the ring (121 is provided. This alignment can also be used for aligning any of the inserts in any of the embodiments by providing outer tabs engaging in predefined slots. Said document describes technical characteristics similar to those described in the previous documents, and with respect to the same, there are the same differences commented in the previous documents.

DESCRIPTION OF THE INVENTION

A fixation system for spinal instrumentation, fundamentally comprising a cap, which houses the head of a screw, the end of said screw projecting through a lower opening of said cap.

A coupling element having two tabs on both side ends rests on the upper part of the head of said screw.

Said coupling element houses an adjusting ring secured to a series of tabs, by which means the movement of the head of said screw can be limited.

The reducing bar is located between said coupling element and the closing lid.

Said cap has threading on its upper, inner part for the fixation of said closing lid.

Said cap has slots on its inner part that start at the bases of the side openings of said cap and end in holes wherein the tabs of said coupling element fit.

The diameter of the head of said screw will always be greater than the diameter of the hole of the lower outlet of said cap.

Said screw has a spherical head with a series of slots separated by 90 degrees, also having in the centermost part thereof a hollow area in the shape of a five-pointed star.

Said screw is cannulated in its interior to enable the passage of a guide wire; the hole of said cannulated screw continues from said hollow.

Said coupling element has a secondary hollow corresponding to the geometry of said adjusting ring and the secured tabs thereof, said secondary hollow formed by a ring secured to a series of slots separated by 90 degrees.

Said closing lid has perimeter threading and a tertiary hollow in the shape of a five-pointed star in the center thereof.

A screwdriver that on the end of the handle has a threaded disc around its perimeter; a rotatable cap that incorporates a lug in the shape of a five-pointed star in the center thereof is secured to the end of said handle for polyaxial fixation of the screw.

A screwdriver that on the end of the handle has a threaded disc around its perimeter; a rotatable cap that incorporates a lug in the shape of a five-pointed star in the center thereof and two horizontal blades with respect to said five-pointed star is secured to the end of said handle for the uniaxial fixation of said screw.

A screwdriver that on the end of the handle has a threaded disc around its perimeter; a rotatable cap that incorporates a lug in the shape of a five-pointed star in the center thereof and two vertical blades with respect to said five-pointed star is secured to the end of said handle for the uniaxial fixation of said screw.

A screwdriver that on the end of the handle has a threaded disc around its perimeter, a rotatable cap that incorporates a lug in the shape of a five-pointed star in the center thereof and four blades separated by 90 degrees with respect to said lug is secured to the end of said handle for the complete locking of said screw.

The present invention provides the following advantages:

With a single screw, it is possible to achieve benefits that up until now required the use of four different types of screws.

Furthermore, once a polyaxial screw is implanted, it can be converted into a fixed or uniaxial screw in any of the different directions thereof.

DESCRIPTION OF THE DRAWINGS

As a complement to the description provided herein, and for the purpose of helping to make the characteristics of the invention more readily understandable, the present specification is accompanied by a series of figures constituting an integral part of the same, which, by way of illustration and not limitation, represent the following.

PREFERRED EMBODIMENT OF THE INVENTION

Figure 1:
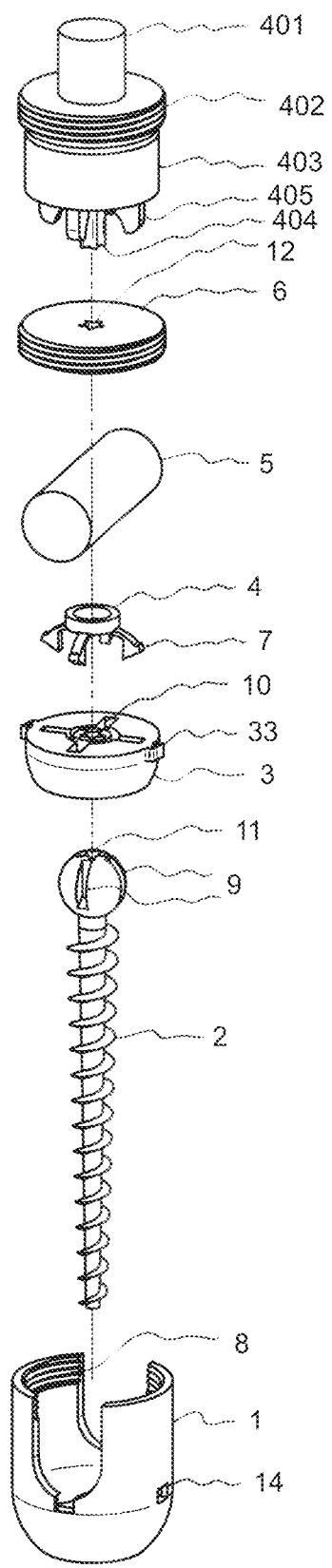
FIG. 1 is an exploded perspective view of the fixation system for spinal instrumentation.
Figure 2:
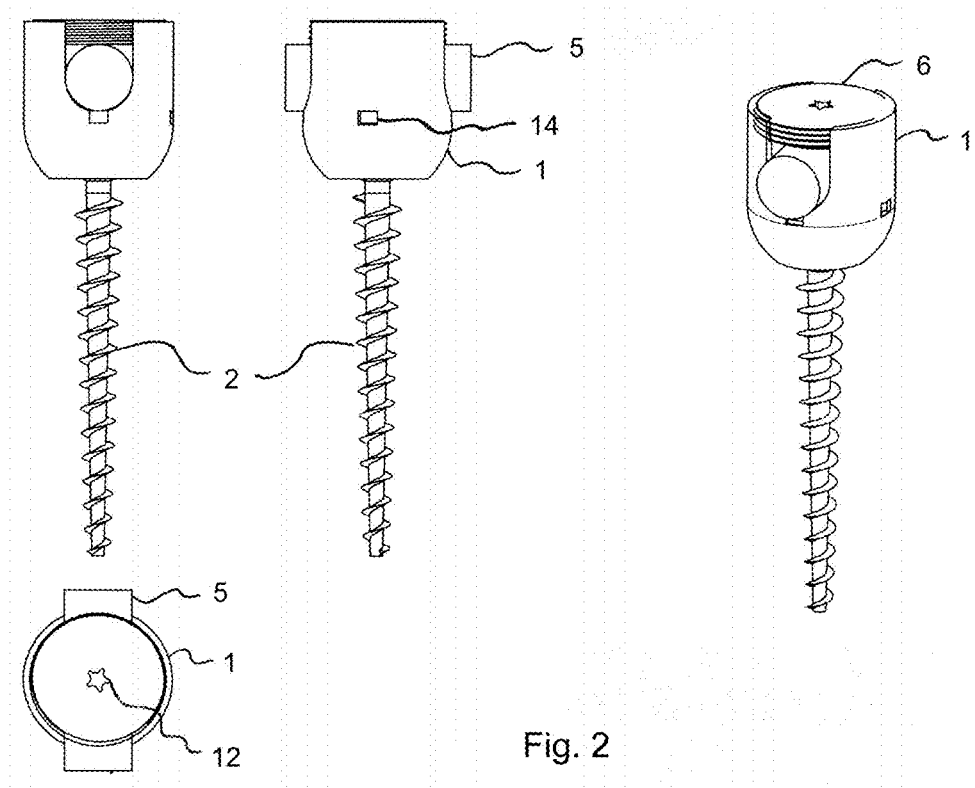
FIG. 2 are views of the set of assembled parts of the fixation system for spinal instrumentation.
Figure 3:
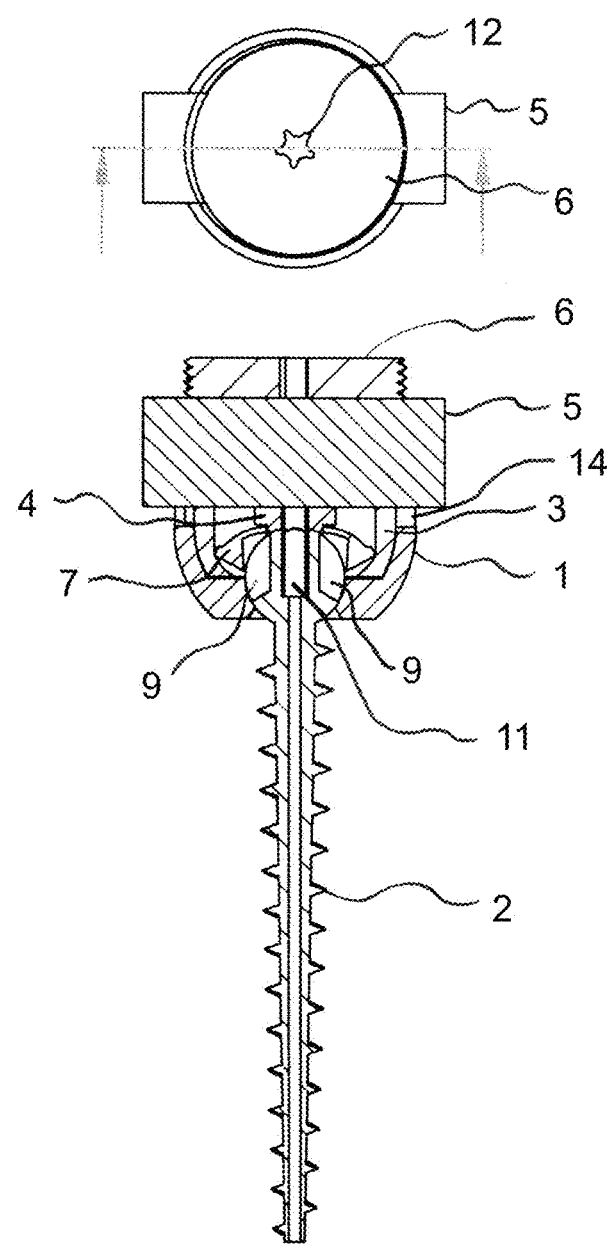
FIG. 3 is a transverse cross section view of the fixation system for spinal instrumentation.
Figure 4:
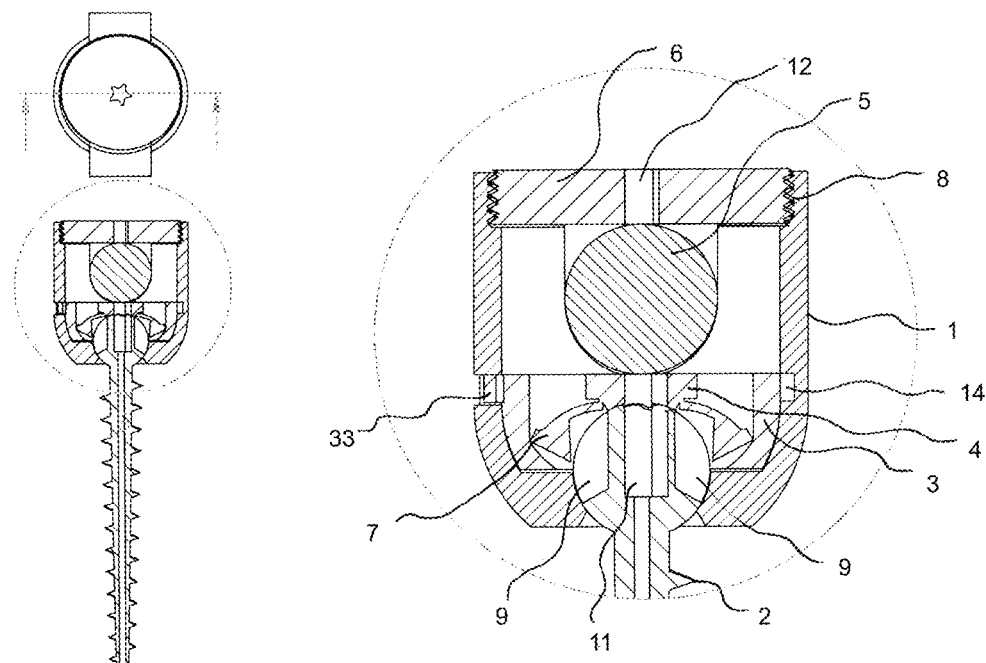
FIG. 4 are transverse cross section views of the fixation system for spinal instrumentation.
Figure 5:
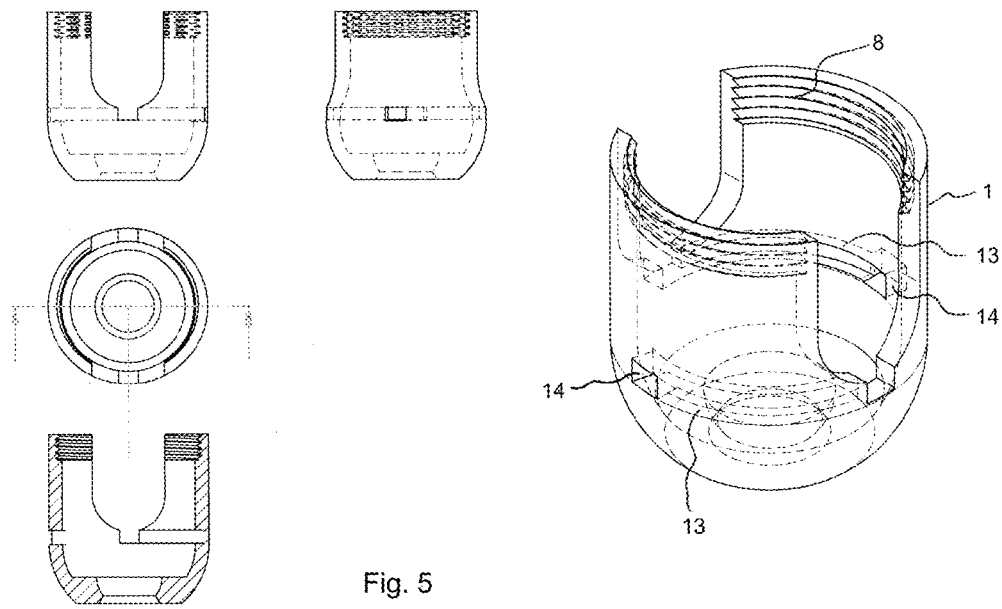
FIG. 5 are views of the cap of the fixation system for spinal instrumentation.
Figure 6:
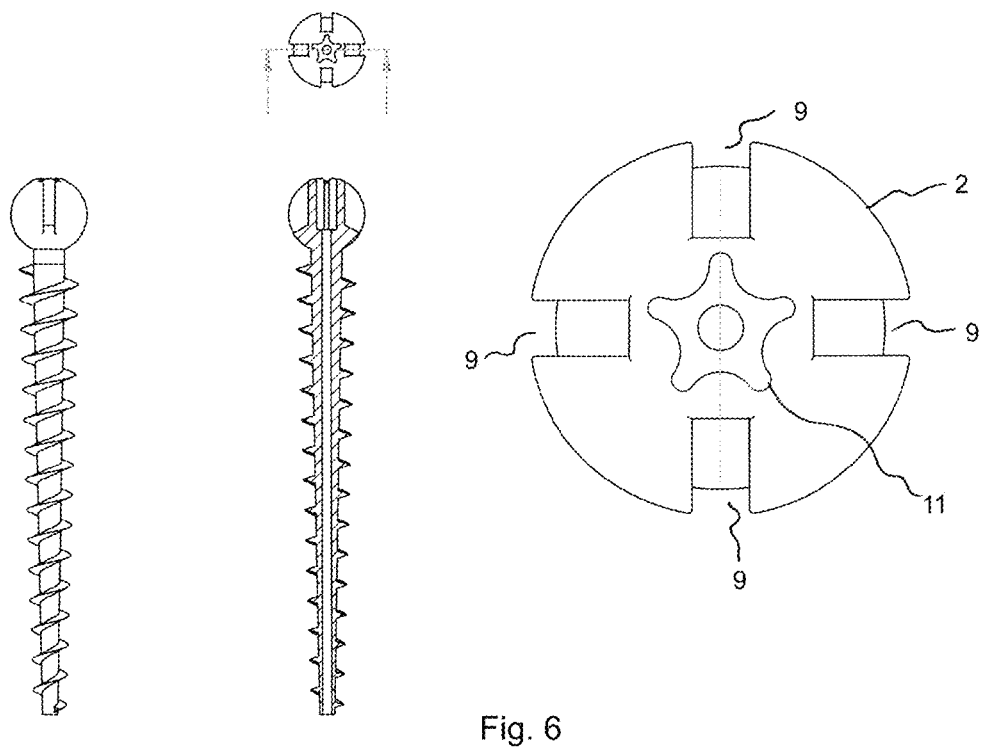
FIG. 6 are views of the screw of the fixation system for spinal instrumentation.
Figure 7:
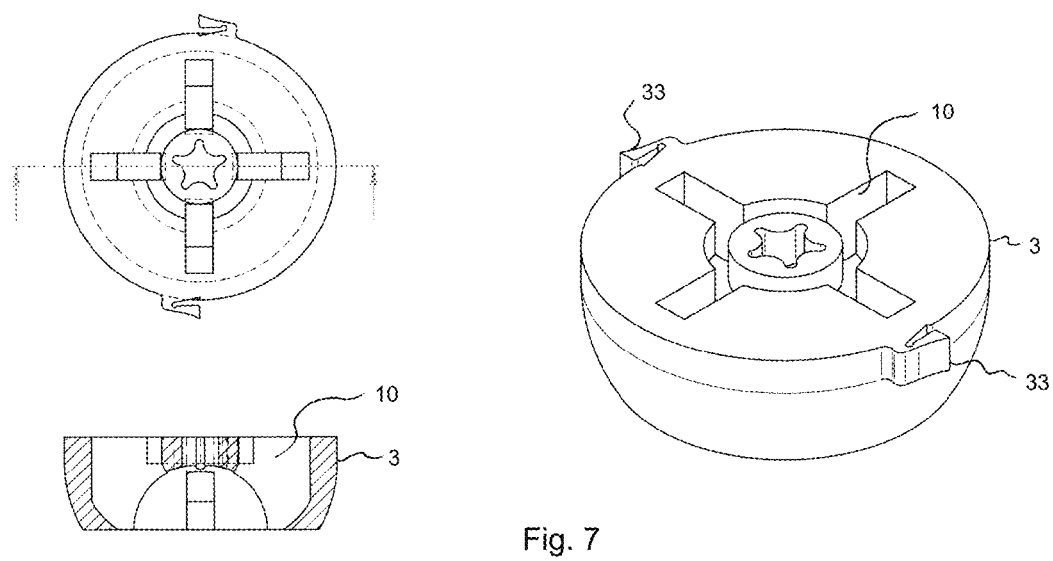
FIG. 7 are views of the coupling element of the fixation system for spinal instrumentation.
Figure 8:
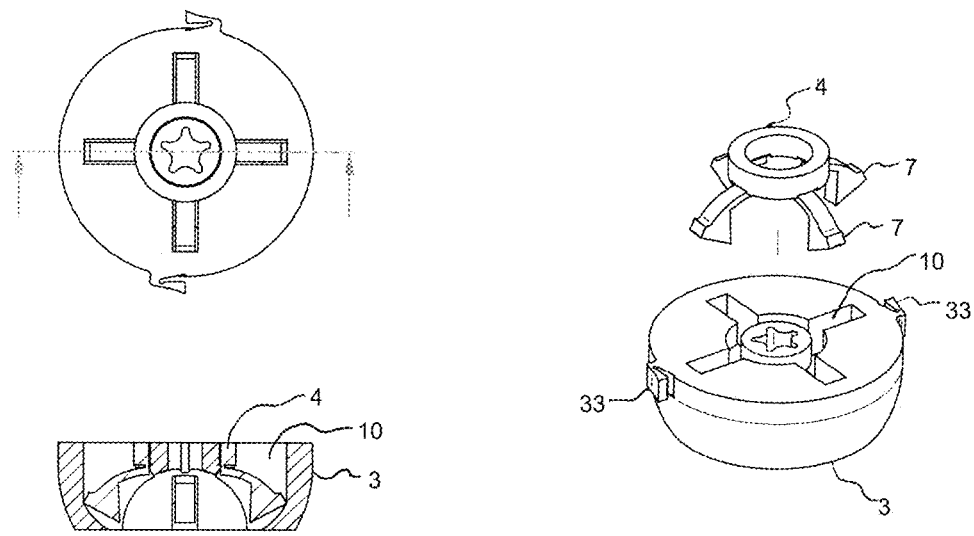
FIG. 8 are views of the coupling element, along with the adjusting ring and the secured tabs of the fixation system for spinal instrumentation.
Figure 9:
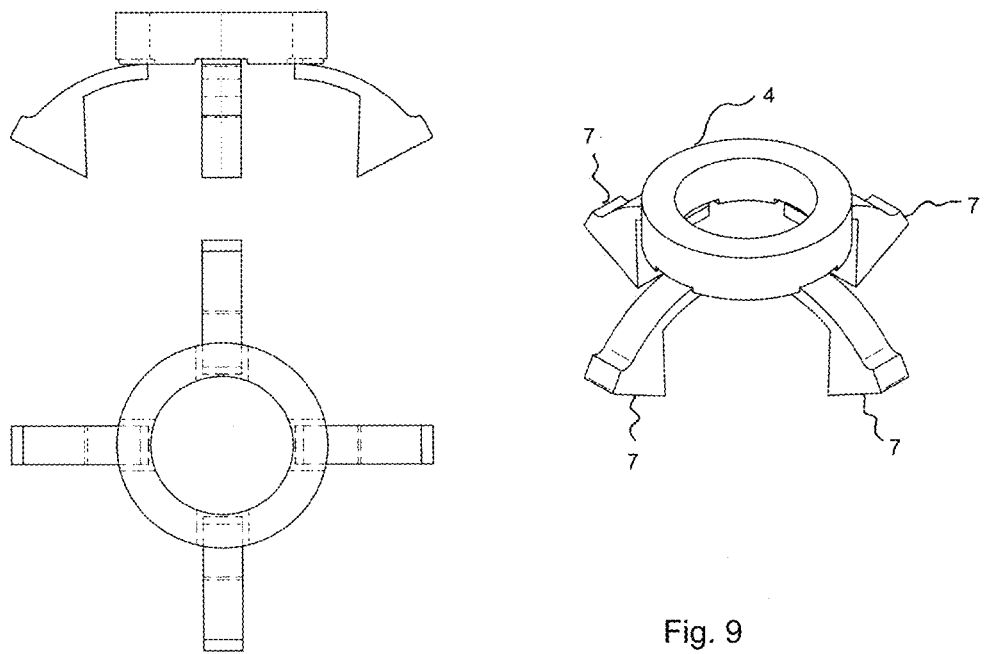
FIG. 9 are views of the adjusting ring of the fixation system for spinal instrumentation.
Figure 10:
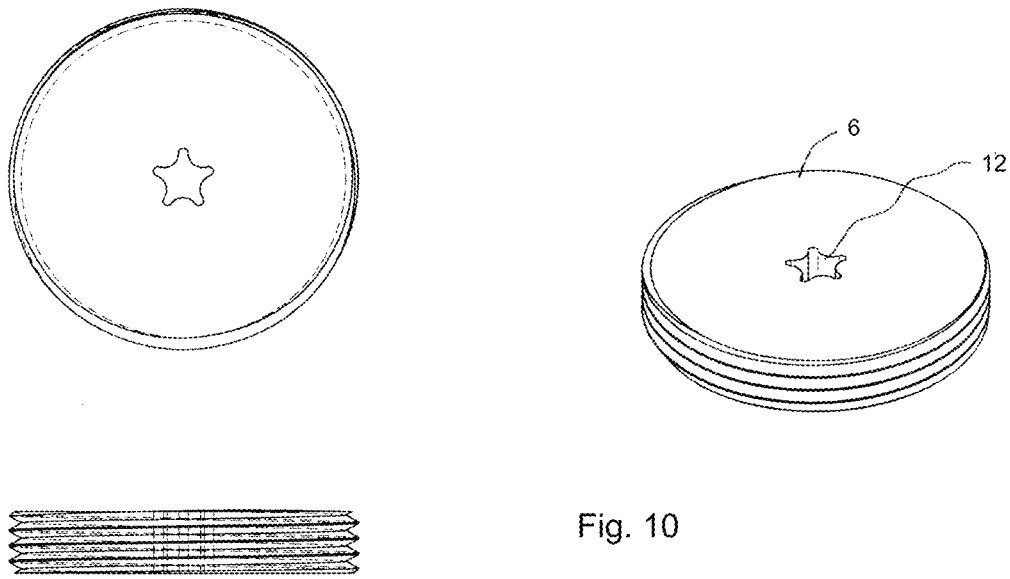
FIG. 10 are views of the closing lid of the fixation system for spinal instrumentation.
Figure 11:
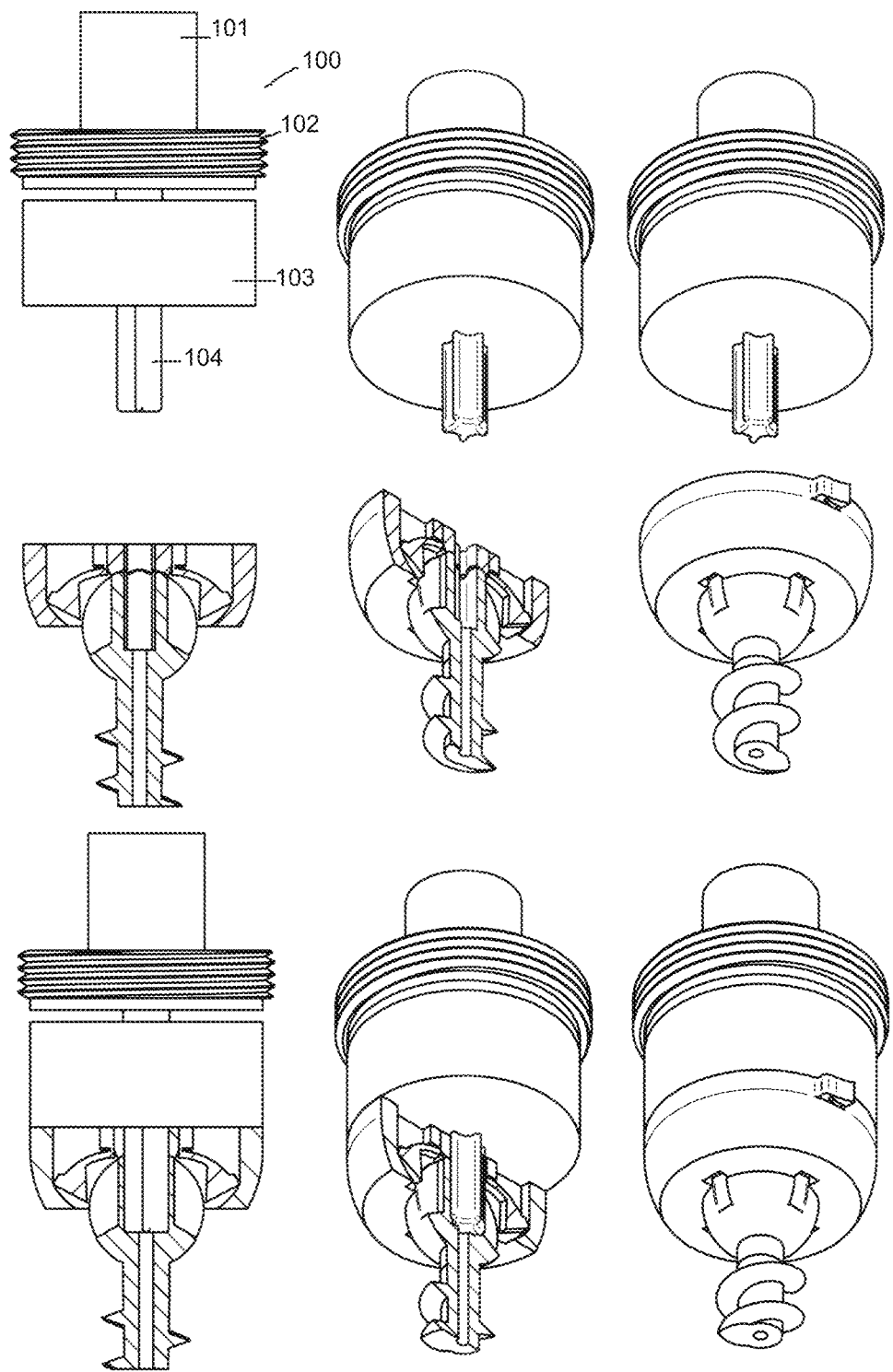
FIG. 11 are views of the fixation system for spinal instrumentation, with an example for polyaxial fixation of the screw.
Figure 12:
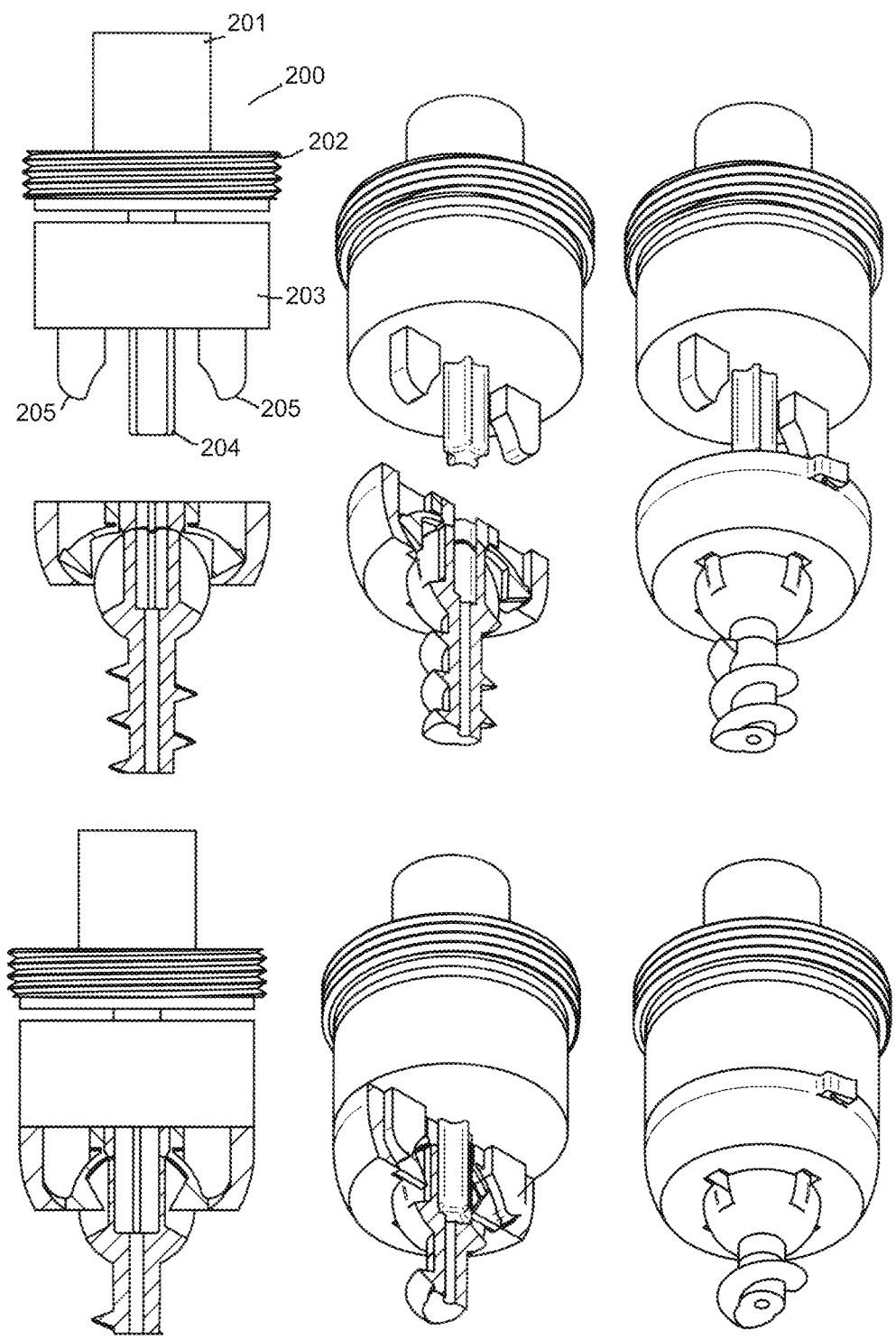
FIG. 12 are views of the fixation system for spinal instrumentation, with an example for uniaxial fixation of the screw.
Figure 13:
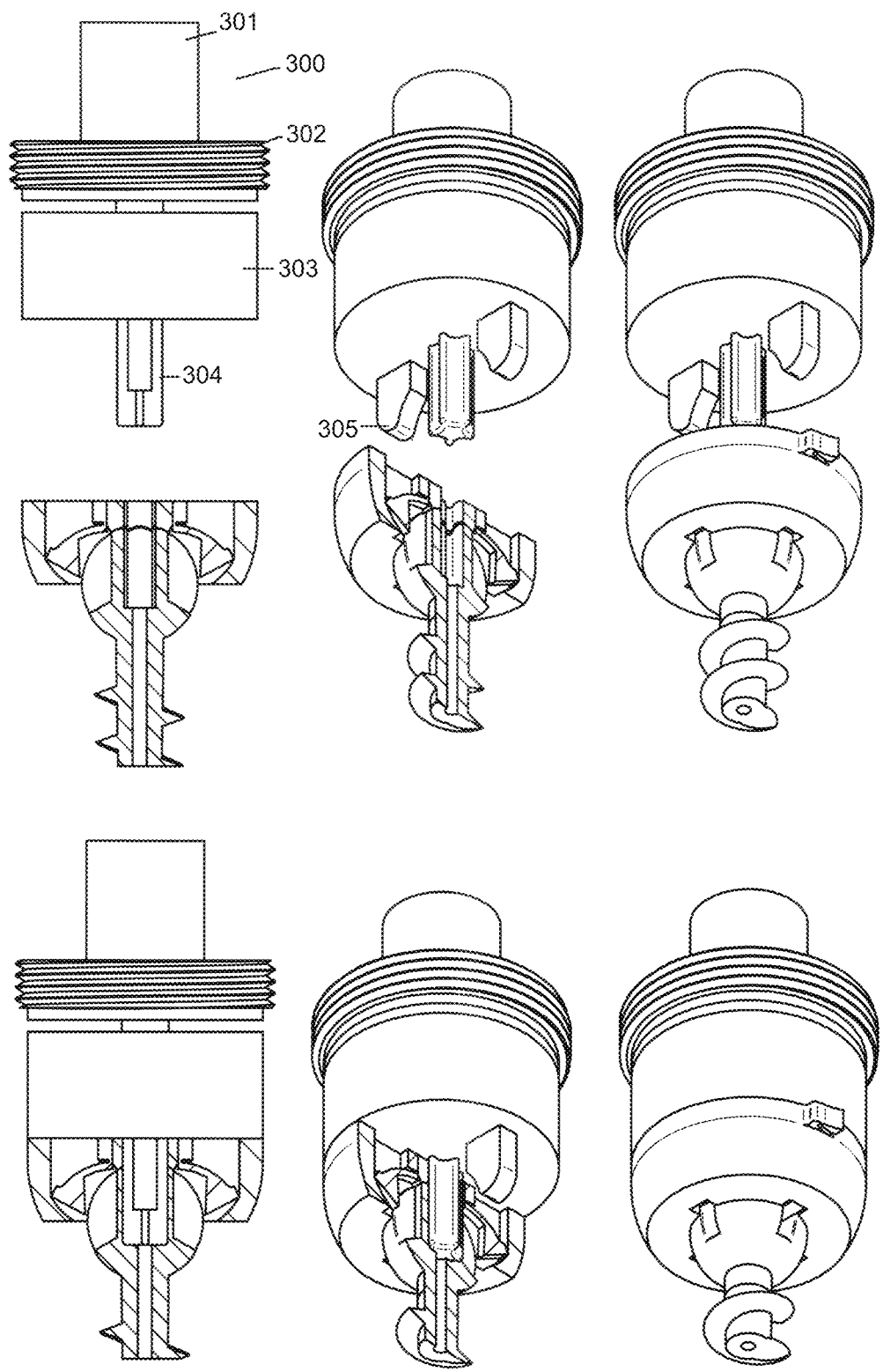
FIG. 13 are views of the fixation system for spinal instrumentation, with an example for uniaxial fixation of the screw.
Figure 14:
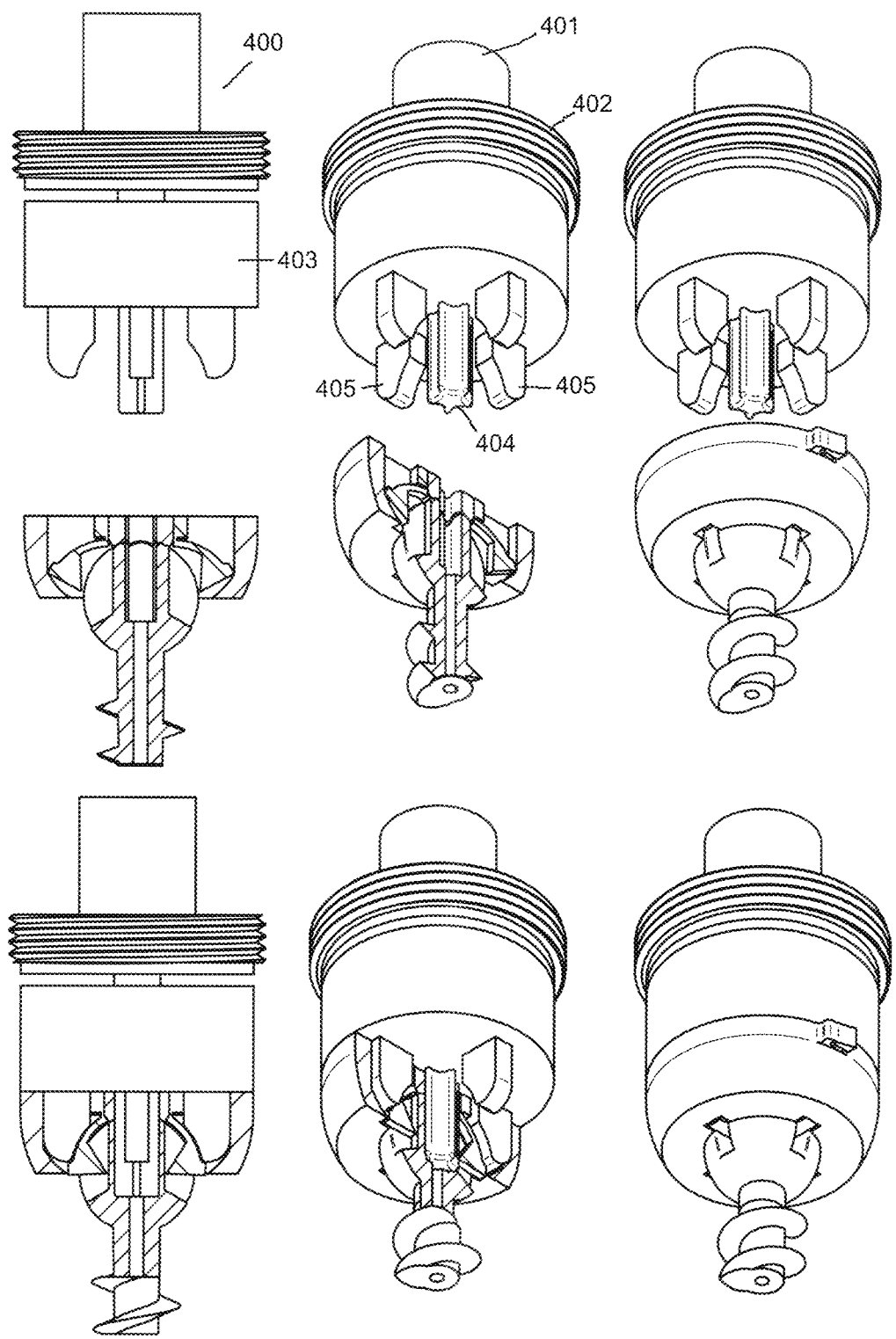
FIG. 14 are views of the fixation system for spinal instrumentation, with an example for the complete locking of the screw.
Figure 15:
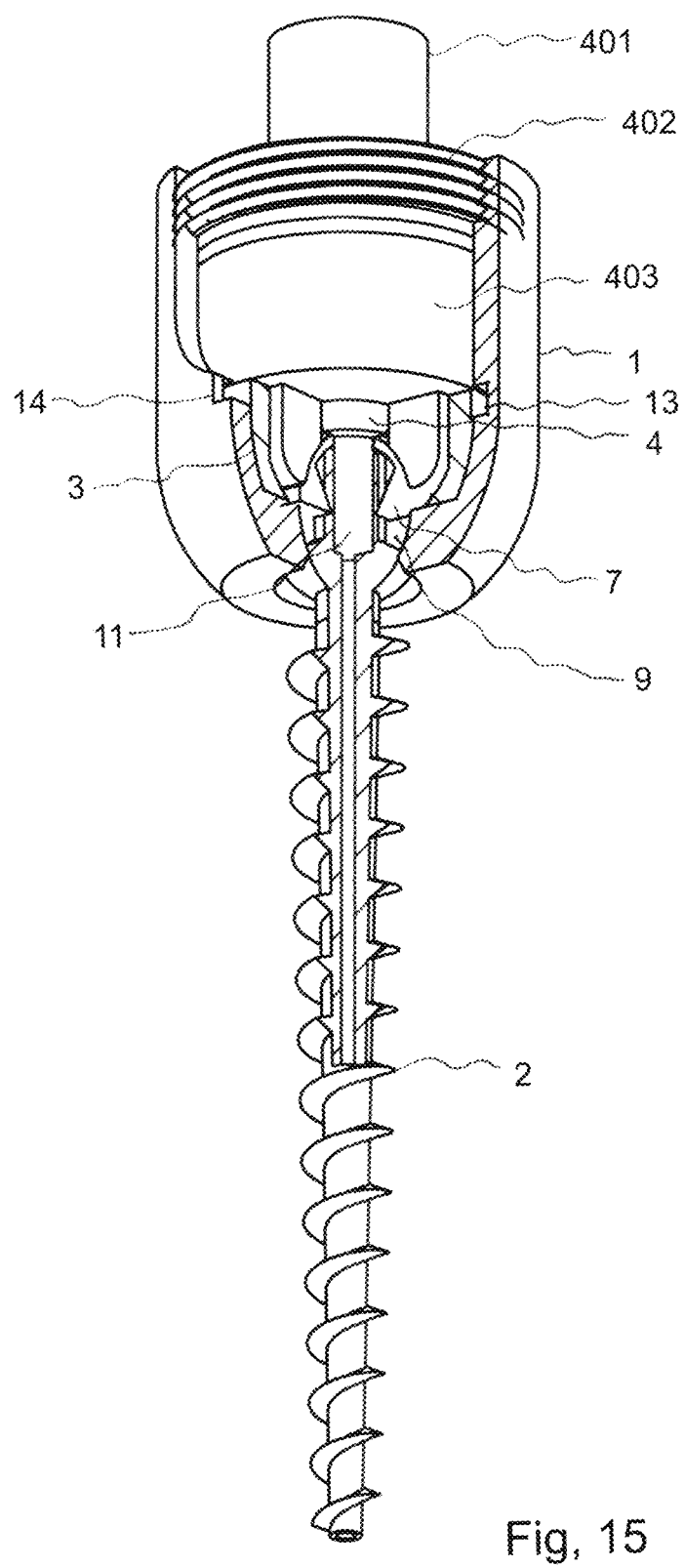
FIG. 15 is a partial cross section perspective view of the total assembly of elements that form the fixation system for spinal instrumentation (during the fixation process).
Figure 16:
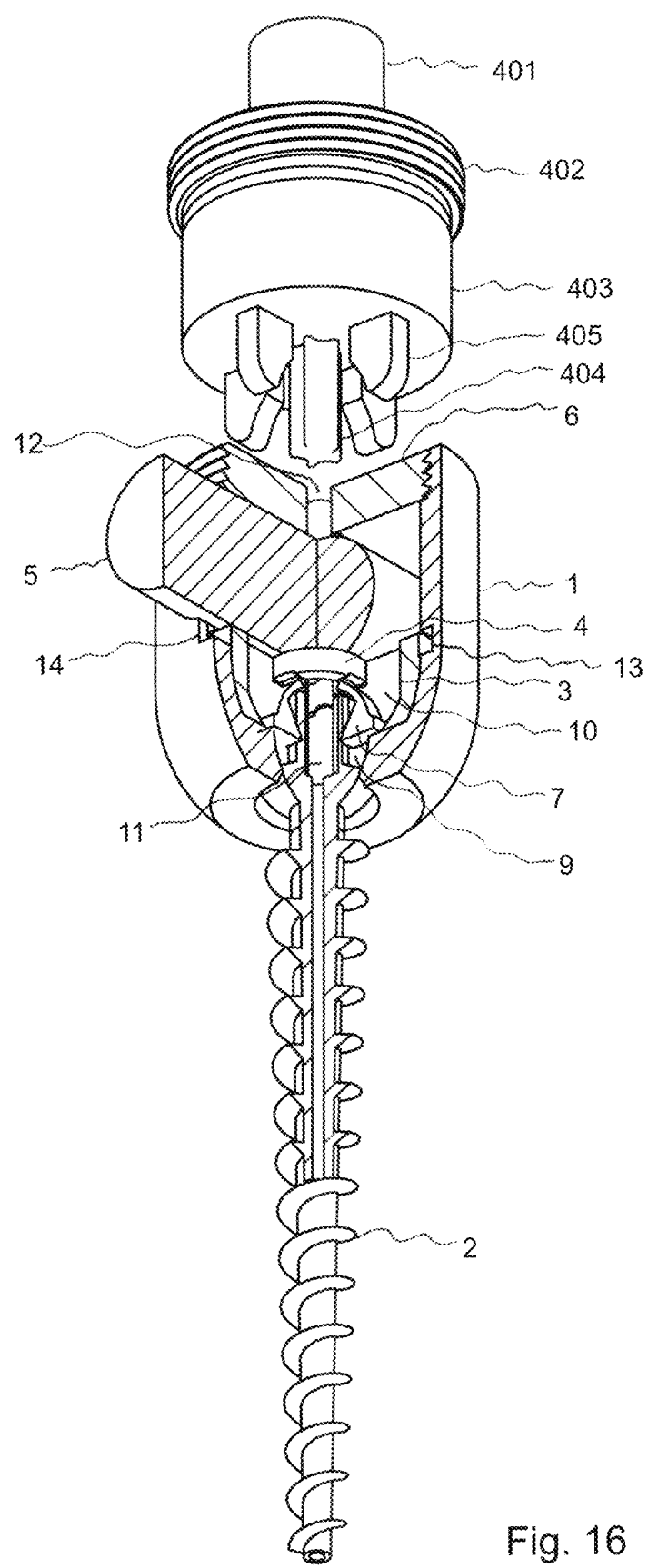
FIG. 16 is a partial cross section perspective view of the total assembly of elements that form the fixation system for spinal instrumentation (once the fixation process has finished).

As can be observed in the attached figures, the fixation system for spinal instrumentation is comprised of a cap (1), which houses the head of a screw (2), the end of said screw (2) projecting through a lower opening of said cap (1).

A coupling element (3) having two tabs (33) on both side ends rests on the upper part of the head of said screw (2).

Said coupling element (3) houses therein an adjusting ring (4) secured to a series of tabs (7), by which means the movement of the head of said screw (2) can be limited.

The reducing bar (5) is located between said coupling element (3) and the closing lid (6).

Said cap (1) has threading (8) on its upper, inner part for the fixation of said closing lid (6).

Said cap (1) has slots (13) on its inner part that start at the bases of the side openings of said cap (1) and end in holes (14) wherein the tabs (33) of said coupling element (3) fit.

The diameter of the head of said screw (2) will always be greater than the diameter of the hole of the lower outlet of said cap (1).

Said screw (2) has a spherical head with a series of slots (9) separated by 90 degrees, also having in the centermost part thereof a hollow area (11) in the shape of a five-pointed star.

Said screw (2) is cannulated in its interior to enable the passage of the guide wire, the hole of said cannulated screw continues from said hollow (11).

Said coupling element (3) has a secondary hollow (10) corresponding to the geometry of said adjusting ring (4) and the secured tabs (7) thereof, said secondary hollow (10) formed by a ring secured to a series of slots separated by 90 degrees.

Said closing lid (6) has perimeter threading and a tertiary hollow (12) in the shape of a five-pointed star in the center thereof.

A screwdriver (100) on the end of the handle (101) has a threaded disc (102) around its perimeter.

A rotatable cap (103) that incorporates a lug (104) in the shape of a five-pointed star in the center thereof is secured to the end of said handle (101) for the polyaxial fixation of the screw (2).

A screwdriver (200) on the end of the handle (201) has a threaded disc (202) around its perimeter.

A rotatable cap (203) that incorporates a lug (204) in the shape of a five-pointed star in the center thereof and two horizontal blades (205) with respect to said five-pointed star is secured to the end of said handle (201) for the uniaxial fixation of said screw (2).

A screwdriver (300) on the end of the handle (301) has a threaded disc (302) around its perimeter.

A rotatable cap (303) that incorporates a lug (304) in the shape of a five-pointed star in the center thereof and two vertical blades (305) with respect to said five-pointed star is secured to the end of said handle (301) for the uniaxial fixation of said screw (2).

A screwdriver (400) in the end of the handle (401) has a threaded disc (402) around its perimeter.

A rotatable cap (403) that incorporates a lug (404) in the shape of a five-pointed star in the center thereof and four blades (405) separated by 90 degrees with respect to said lug (404) is secured to the end of said handle (401) for the complete locking of said screw (2).

Examples of use of the fixation system for spinal instrumentation:

For the polyaxial fixation of the screw (2), when it is required that the cap (1) be moved in any direction to search for the reducing bar (5) (without forcing the vertebra towards that direction).

For the uniaxial fixation of the screw (2), when it is required that the screw (2) be only able to move in a sagittal direction and not in other directions; for example, when it is adapted to a curve in the sagittal plane in kyphosis and we would like the head to be able to move on this plane but we do not want movements of the screw (vertebra) on the transverse plane.

For the uniaxial fixation of the screw (2), when it is required that the screw (2) be able to move in a transverse but not sagittal direction; for example, when there is a purely transverse movement but it is not on the sagittal plane.

For the complete fixation of the screw (2), when it is required that the vertebra remains fixed at a point without moving on any plane, we want the reducing bar (5) to search for the screw and not vice versa.

In general, all of these movements are already possible with the screws existing on the market, however, for each one of these situations we would need a different screw. Here, we have the opportunity to achieve this with only one screw being able to determine in advance or even a priori how we want it to act.

Having sufficiently described the nature of the present invention, in addition to an example of implementation, it must be added that the shape and materials of said invention may be modified, provided that it does not imply altering the characteristics claimed below.

The invention claimed is:

1. A fixation system for spinal instrumentation comprising:
   a cap having an upper, inner part comprising threading, and a lower inner part comprising two slots extending about a perimeter of the lower inner part of the cap, in which an end of each of the two slots has a hole and a central opening;
   a screw having a head with four slots and a body having a first end connected to the head and a second end;
   a coupling element, and two opposing radial tabs extending from a periphery of the coupling element, the coupling element resting on an upper part of the head of the screw, such that the opposing radial tabs engage the holes of the cap;
   an adjusting ring comprising a plurality of radially extending tabs received by radial apertures of the coupling element, wherein the plurality of tabs limit movement of the head of the screw;
   a closing lid comprising a circumferential perimeter threading complementary to the upper inner part threading of the cap, wherein the closing lid is connected to the cap via the circumferential perimeter threading engaging the upper inner part threading of the cap;
   a reducing bar, wherein the reducing bar is located between the coupling element and the closing lid;
   a screwdriver for polyaxial fixation of the screw;
   a screwdriver for uniaxial coronal fixation of the screw;
   a screwdriver for uniaxial sagittal fixation of the screw; and
   a screwdriver for complete locking of the screw
   wherein the cap houses the head of the screw, and the second end of the screw projects through the central opening of the cap.

2. The fixation system for spinal instrumentation according to claim 1, wherein:
   a diameter of the head of the screw is greater than a diameter of the central opening of the cap;
   the screw having a spherical head with a series of four slots, the series of four slots each separated by 90 degrees, and wherein a centermost part of the screw has a hollow area in a five-pointed star shape; and
   the screw comprising a cannulated interior, and a screw hole connected to the hollow area of the screw, enabling passage of a guide wire.

3. The fixation system for spinal instrumentation according to claim 1, wherein the adjusting ring fits inside of the coupling element and the extending tabs of the adjusting ring are secured to a series of slots separated by 90 degrees.

4. The fixation system for spinal instrumentation according to claim 1, further comprising a tertiary hollow in a shape of a five-pointed star in a center thereof.

5. The fixation system for spinal instrumentation according to claim 1, wherein the screwdriver comprises an end with a handle, the end of the handle further comprising a threaded disc around a perimeter; a rotatable cap having a lug in a shape of a five-pointed star in a center thereof, secured to the end of the handle allowing the placement of the screw without displacing the tabs of the adjusting ring, leaving the head of the screw unlocked, for the polyaxial fixation of the screw.

6. The fixation system for spinal instrumentation according to claim 1, wherein the screwdriver for uniaxial coronal fixation of the screw comprises an end with a handle, the end of the handle comprising a threaded disc around a perimeter; a rotatable cap having a lug in a shape of a five-pointed star in a center thereof, and two horizontal blades with respect to the five-pointed star secured to the end of the handle, whereby when the screwdriver is locked to the screw, and to the cap, the blades being forced downwards, such that the tabs of the adjusting ring engage the slots of the screw head, allowing movement of the screw, in relation to the cap, in only one direction for the uniaxial transverse fixation of the screw.

7. The fixation system for spinal instrumentation according to claim 1, wherein the screwdriver for uniaxial sagittal fixation of the screw comprises an end with a handle, the end of the handle comprising a threaded disc around a perimeter; a rotatable cap having a lug in a shape of a five-pointed star in a center thereof, and two vertical blades with respect to the five-pointed star secured to the end of the handle, the two vertical blades being placed perpendicular to the screwdriver for uniaxial coronal fixation of the screw, such that the vertical blades descend and the tabs of the adjusting ring engage the slots of the head of the screw, allowing movement of the screw in relation to the cap in one direction and perpendicular to an axis for the uniaxial sagittal fixation of the screw.

8. The fixation system for spinal instrumentation according to claim 1, wherein the screwdriver for complete locking of the screw comprises an end with a handle, the end of the handle further comprising a threaded disc around a perimeter; a rotatable cap having a lug in a shape of a five-pointed star in a center thereof, and four blades separated by 90 degrees secured to the end of the handle for the complete locking of the screw.

* * * * *